United States Patent [19]

Troutner et al.

[11] Patent Number: 4,486,189

[45] Date of Patent: * Dec. 4, 1984

[54] DUAL MODE HEMODIALYSIS SYSTEM

[75] Inventors: Vernon H. Troutner, St. Petersburg; Richard A. Morrow, Tarpon Springs, both of Fla.

[73] Assignee: Extracorporeal Medical Specialties, Inc., King of Prussia, Pa.

[ * ] Notice: The portion of the term of this patent subsequent to Aug. 7, 2001 has been disclaimed.

[21] Appl. No.: 423,376

[22] Filed: Sep. 24, 1982

[51] Int. Cl.³ .............................................. A61M 1/03
[52] U.S. Cl. .................................... 604/5; 128/DIG. 3
[58] Field of Search ................. 604/4, 5; 128/DIG. 3; 210/321.2, 321.3

[56] References Cited

U.S. PATENT DOCUMENTS

| 3,756,234 | 9/1973 | Kopp | 128/214 R |
|---|---|---|---|
| 3,830,234 | 8/1974 | Kopp | 128/214 R |
| 3,848,592 | 11/1974 | Willock | 128/214 R |
| 3,982,535 | 9/1976 | Bahrton | 604/5 |
| 3,985,134 | 10/1976 | Lissot et al. | 128/214 R |
| 4,048,064 | 9/1977 | Clark | 604/5 X |
| 4,231,366 | 11/1980 | Schael | 128/214 E |

FOREIGN PATENT DOCUMENTS 2636290  2/1978  Fed. Rep. of Germany .......... 604/5

OTHER PUBLICATIONS

"New System for Single-Needle Dialysis", British Medical Journal, vol. 281, p. 1109 (Oct. 25, 1980).

Primary Examiner—Edward M. Coven
Attorney, Agent, or Firm—Mark A. Hofer

[57] ABSTRACT

A hemodialysis system capable of operation in either a single needle mode or a double needle mode includes an arterial blood pump which is the sole blood pump in the system during the double needle mode. For single needle mode operation a venous blood pump is employed to return blood to the patient. A pump speed control adjusts the speed of the arterial pump in the double needle mode, and the speeds of both blood pumps in the single needle mode. A controller continuously operates the arterial pump in the double needle mode, and alternately activates the two pumps in the single needle mode. A module for modifying a commercially available double needle system for operation in either of the two modes is also described.

6 Claims, 3 Drawing Figures

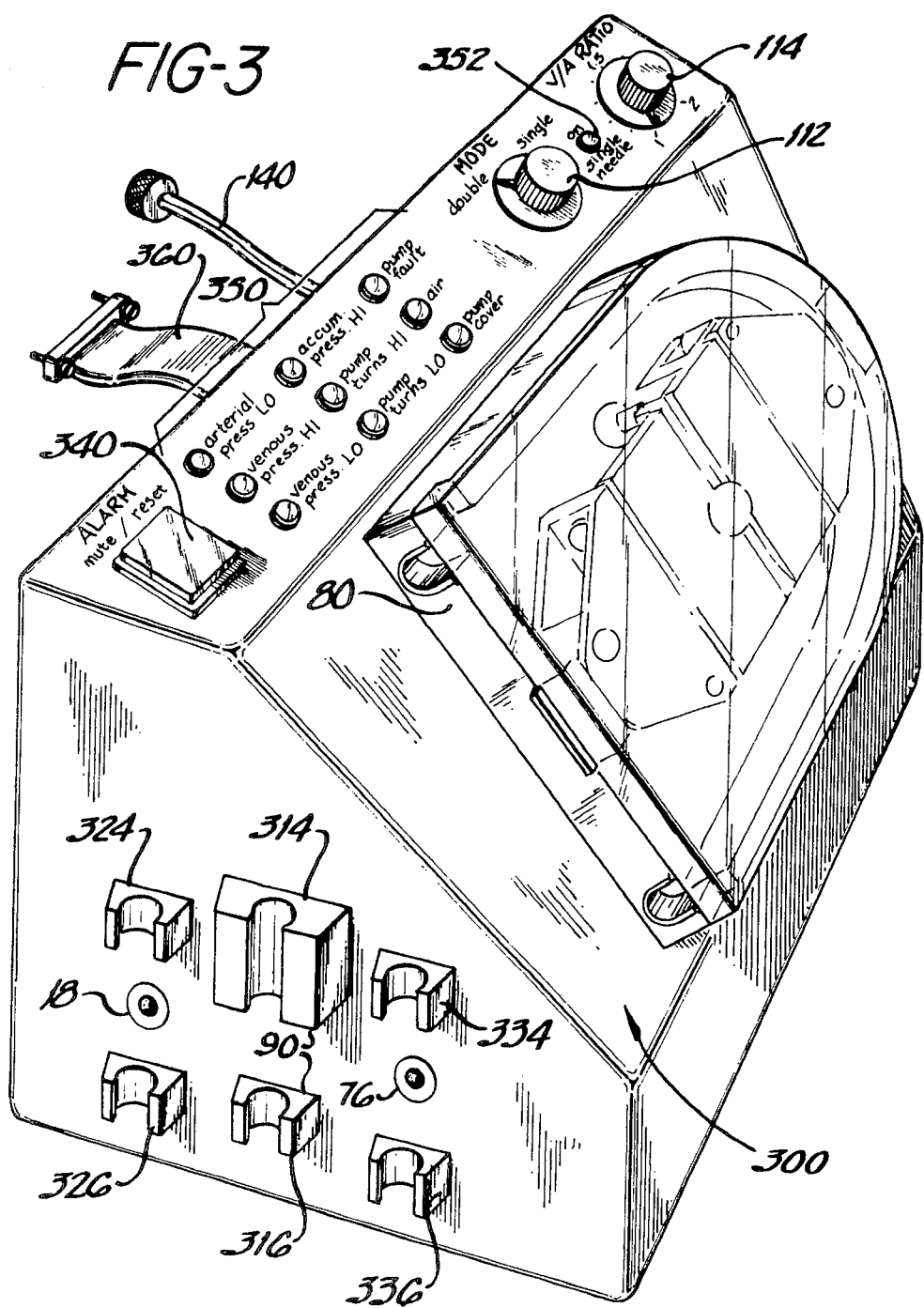

DUAL MODE HEMODIALYSIS SYSTEM

This invention relates to hemodialysis systems which perform extracorporeal blood purification and, in particular, to hemodialysis systems which are operable with either two needles or a single needle for the transfer of blood from and to the patient.

Hemodialysis blood flow systems are employed as a therapeutic measure when a patient's kidneys no longer perform their blood purifying function by reason of disease, removal or other malfunction. Kidney failure results in the accumulation of toxic wastes in the patient's blood. Unless measures are taken to remove these wastes, the patient will experience potentially fatal uremic poisoning. Uremic poisoning may be prevented through the use of hemodialysis, by which blood is drawn from the patient and circulated through a dialyzer. In the dialyzer, the blood is separated from a specially treated dialysate fluid by a membrane which has pores of microscopic size through which waste products from the blood may pass. The microscopic pores are too small, however, to permit the passage of blood cells, proteins, and other essential elements of the blood through the membrane. The waste products thus diffuse into the dialysate fluid and are removed from the patient's blood. The purified blood is then returned to the patient's body.

In many conventional hemodialysis systems, such as the Single Patient System (SPS) Model DM-350 produced by Extracorporeal Inc. of King of Prussia, Pa., blood is extracted from the patient through a first arterial venipuncture, which may typically be formed in a cannulation procedure. The blood is then processed by the SPS system and returned to the patient's body through a second, venous venipuncture, which may also comprise a cannula.

In other known hemodialysis systems, blood is extracted from and returned to the patient's circulatory system through a single needle with a Y-shaped junction. In such a hemodialysis system, blood may be alternately cycled from and to the patient's body by arterial and venous blood pumps, respectively. During the first, or arterial, phase of operation, blood is drawn from the patient and pumped into the dialysis system by the arterial blood pump. Blood is prevented from returning to the needle by the closure of a valve located between the outlet of the arterial pump and the needle or by a clamping action of the venous blood pump. Blood pressure within the system builds until a time at which the arterial pump is turned off, the valve is opened or the venous pump in a two-pump system is turned on to pump blood out of the dialysis system and back to the patient during a second, venous phase of operation. After the return of a desired amount of blood to the patient, the venous phase is terminated and the cycle repeats.

Each type of hemodialysis system has advantages which can vary from patient to patient. For instance, the single needle system offers the advantage of half the number of needle insertions, which may be psychologically attractive to the patient, as well as possibly prolonging the life of the fistula into which the needle is normally inserted. However, if a patient has low blood flow rates, hemodialysis through a single needle may not be practical, and the use of a double needle system may be necessitated. In addition, single needle systems frequently require larger needles which are difficult to insert, and blood recirculation through the hemodialysis system may be high if blood flow through the fistula is low. It is therefore desirable for a hemodialysis system to be capable of operation in either a single needle mode or a double needle mode so as to be of use to a wider variety of patients. In accordance with the principles of the present invention a hemodialysis system is provided which is capable of operation in either a single needle mode or a double needle mode. The system can be operated in either the single or double needle mode by setting a mode selector switch. Changing from one mode to the other is both simple and convenient for the user. The system includes an arterial blood pump as the sole blood pump in the double needle mode, which pumps blood into the dialyzer from the patient's artery. Blood pressure established by the arterial blood pump is monitored as a safety control precaution, and this pressure causes the blood to flow out of the system and back to the patient's vein. A speed control is provided to adjust the speed of the arterial pump and hence the blood flowrate in the double needle mode.

When system operation is switched to the single needle mode, a second, venous blood pump is employed in combination with the arterial blood pump. The speed control now adjusts the speeds of both pumps to give the desired blood flowrate. A ratio control is also provided to adjust the ratio of the venous to arterial pump speeds. A monitor and control arrangement automatically adjusts the pump speeds to provide the proper ratio. The previously mentioned blood pressure monitor is utilized in a preferred embodiment in combination with a venous pump monitor to enable the monitor and control arrangement to alternately activate the two pumps. Those elements necessary to modify a commercially available double needle system for both single and double needle operation may conveniently be arranged in modular form.

In the drawings:

FIG. 3 illustrates a module constructed in accordance with the principles of the present invention for modifying the commercially available SPS hemodialysis system Model DM-350 for operation as a single needle system.

Figure 1:
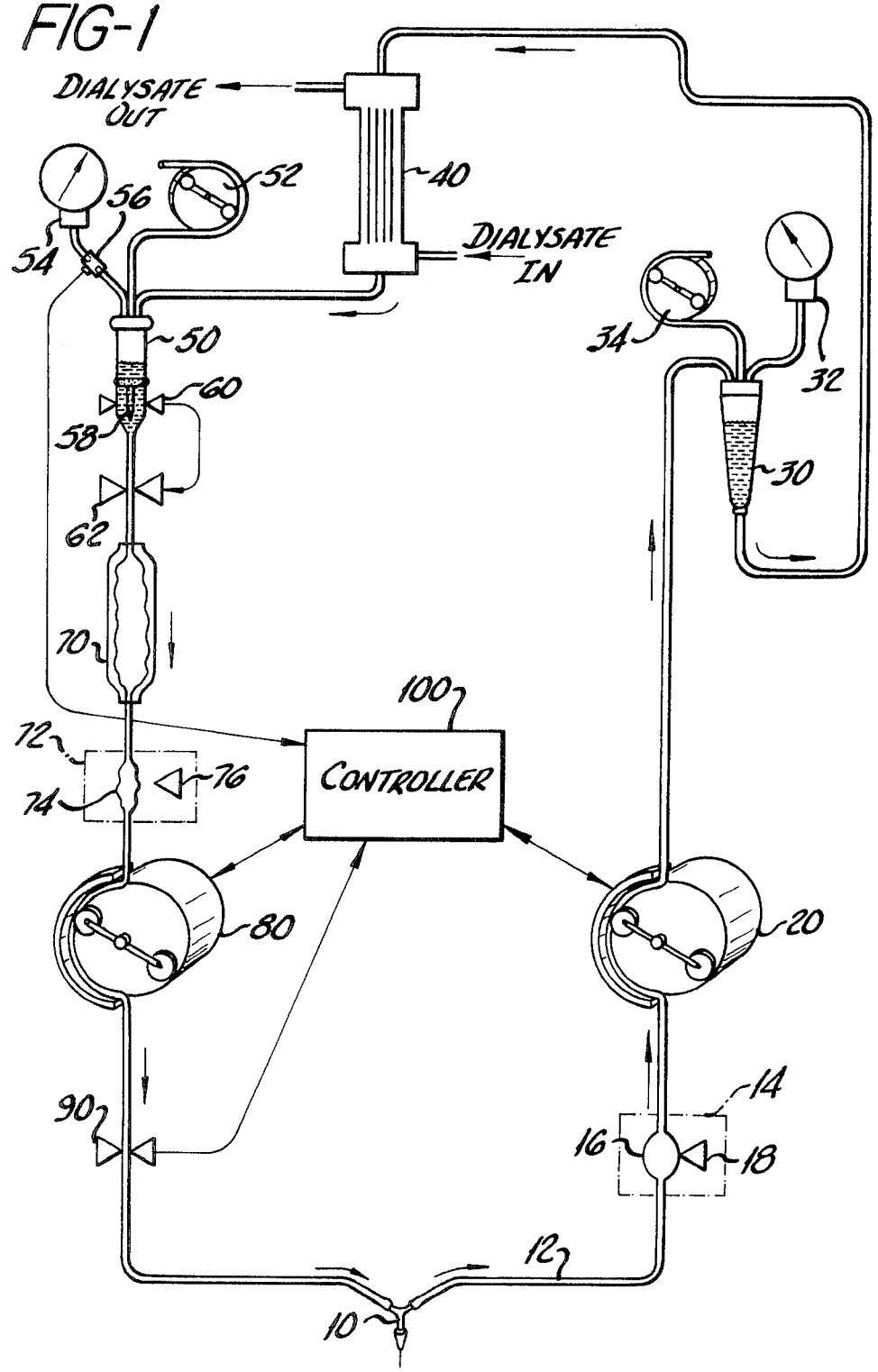
FIG. 1 illustrates the blood circulation path of a hemodialysis system constructed in accordance with the principles of the present invention.

Referring to FIG. 1, the blood flow path of a single needle hemodialysis system is shown, including a single needle 10 suitable for the transfer of blood from and to a patient. In FIG. 1, the arrows indicate the direction of the flow of blood through the system.

From the single needle 10, blood flows through the blood tubing 12 to a negative pressure pillow switch 14. The pillow switch 14 includes a pillow-like section of tubing 16 and a sensor or switch 18 which is responsive to a relaxation of pressure in the pillow-like section 16. When the pillow pressure declines below a certain level the sensor or switch responds by initiating a system alarm as well as other procedures which interrupt the operation of the system.

From the pillow switch 14 the blood tubing is connected through an arterial roller blood pump 20. The arterial blood pump 20 operates under control of a controller 100, as will be described subsequently. The blood tubing is then connected to a post-pump arterial drip chamber 30 which collects blood and accommodates the connection of various gauges to the system. The pressure in the drip chamber 30 is monitored by an arterial mechanical gauge 32 with alarm contacts. The blood level within the chamber 30 may be varied through the operation of a blood level adjust roller pump 34, by which air may be added to or subtracted from the chamber. The outlet of the drip chamber 30 is connected by blood tubing to the inlet of a capillary dialyzer 40. In the dialyzer, impurities in the blood pass through the dialyzer membrane and into dialysate fluid, which flows into and out of the dialyzer through separate ports under control of a dialysate preparation system (not shown).

Purified blood flows out of the dialyzer 40 and into a venous drip chamber 50. The pressure within the venous drip chamber 50 is monitored by a mechanical venous pressure gauge 54 with alarm contacts. A second blood level adjust pump 52 is connected to the drip chamber 50 to add or subtract air from the chamber, thereby adjusting the blood level within the chamber. In the tubing line between the venous drip chamber 50 and the venous pressure gauge 54 is a solid state pressure transducer 56 which controls the cycling of the blood pumps and also provides another monitor of venous blood pressure. The venous drip chamber 50 further includes a filter 58 located within the chamber.

An air/foam detector 60 is located next to the venous drip chamber 50. The detector 60 ultrasonically or optically detects the presence of an abnormal amount of air or foam in the blood and also monitors the blood level in the chamber 50. The detector responds to the occurence of such an abnormality by activating a clamp 62, which clamps the blood tubing closed to prevent the pumping of foam and air bubbles into the patient's circulatory system.

The blood tubing is then connected to the inlet of a vinyl accumulator bag 70. The outlet of the accumulator bag 70 is coupled to a positive pressure pillow switch 72, which may be merely an extension of the accumulator bag 70 or, as shown in FIG. 1, may include its own pillow-shaped tubing section 74. Abnormal expansion of the pillow-shaped section 74 in response to an undesirable buildup of blood pressure causes the sensor or switch portion 76 to set off an alarm and to interrupt system operation.

From the pillow switch 72 the blood tubing passes through a venous roller blood pump 80 which is operated under control of the controller 100. The blood tubing then passes through a second air/foam detector 90, which is connected into the system alarm by the controller 100. Finally, the blood tubing is connected to the needle 10 to return the purified blood to the patient's circulatory system. The arrangement of FIG. 1 is described in further detail in concurrently filed U.S. patent application Ser. No. 423,380, entitled "Single Needle Alternating Blood Flow System".

Figure 2:
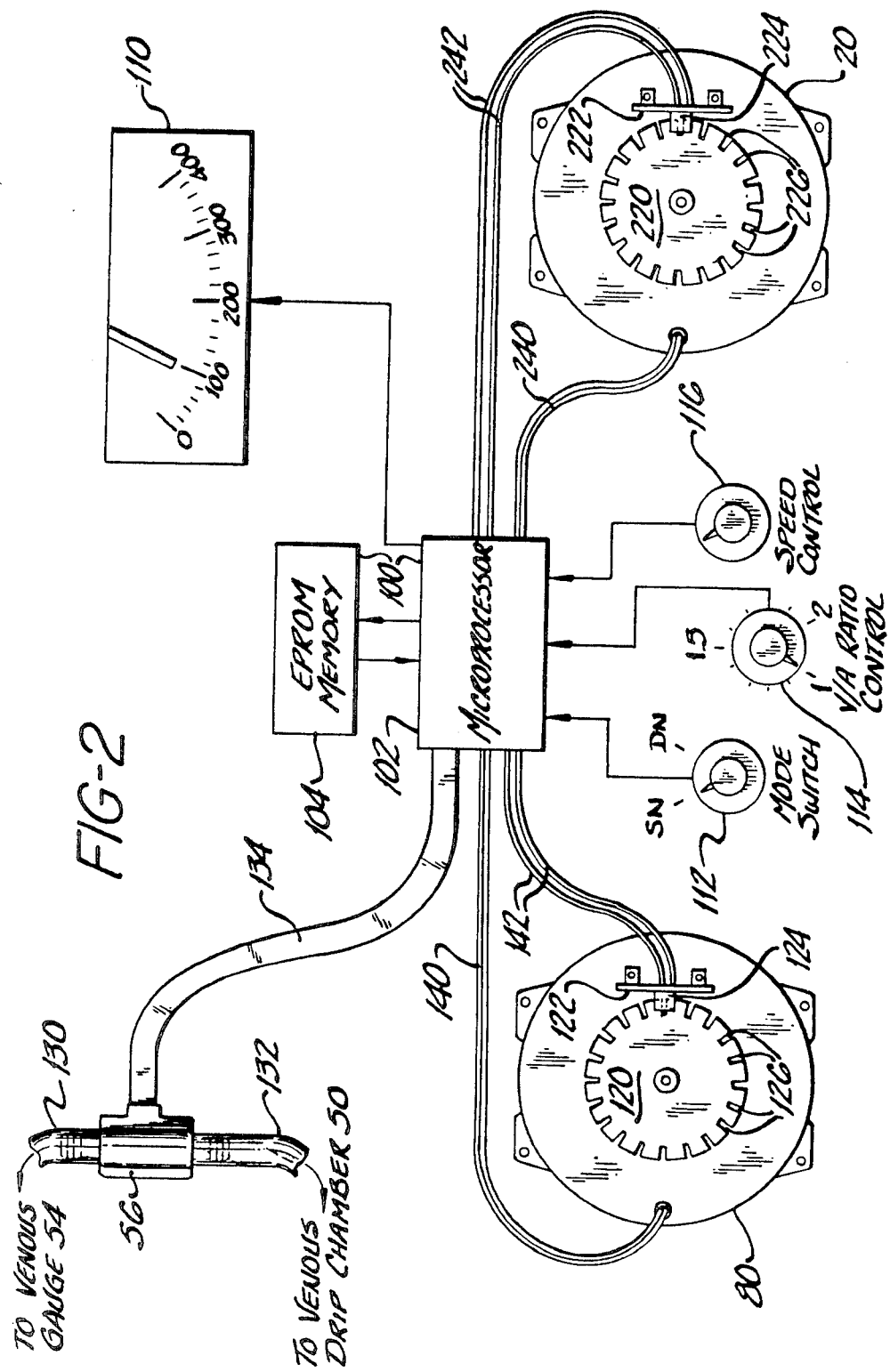
FIG. 2 illustrates in greater detail the control system for the venous and arterial blood pumps of the arrangement of FIG. 1.

The control arrangement for the venous and arterial pumps of FIG. 1 is shown in greater detail in FIG. 2. The solid state pressure transducer 56 has one port connected by way of a tubing segment 130 to the venous pressure gauge 54 (not shown in FIG. 2), and a second port connected by way of a tubing segment 132 to the venous drip chamber 50 (not shown in FIG. 2). The pressure transducer 56 is illustrated as a flow-through type comprising an open-ended tube located between the two ports. A silicon chip sensing element is bonded to the side of the tube, and contains a sensing diaphragm and piezoresistors. As the pressure within the tube changes, the diaphragm flexes, changing the resistance of the piezoresistors and resulting in an output voltage proportional to pressure. This output voltage is communicated to an input of microprocessor 102 of controller 100 by way of a cable 134.

Outputs of the microprocessor 102 are coupled to the motor of arterial pump 20 by a power cable 240 and to the motor of venous pump 80 by a power cable 140. The microprocessor 102 is also connected to the arterial and venous pumps by wires 242 and 142, respectively. The wires 242 and 142 convey motor speed information to the microprocessor from slot encoders connected to the shafts of the pump motors. Each slot encoder includes a slotted disc 120, 220 mounted on the shaft of the pump motor, an optical detector 124, 224 and a circuit board 122, 222. As each slotted disc 120, 220 turns on the motor shaft, the slots 126, 226 along the perimeter of the disc are sensed by optical detectors 124, 224, respectively, and are indicated by pulses produced by circuitry on respective circuit boards 122, 222. The pulses are applied to the microprocessor 102 by way of wires 142, 242, thereby providing the microprocessor with an indication of the motor speeds of the arterial and venous pumps.

The mocroprocessor 102 also receives input signal information from a mode switch 112, a venous/arterial ratio control 114, and a speed control 116. The information received by the microprocessor 102 is used as data for a control program stored in an EPROM memory 104, which is connected to the microprocessor 102. The microprocessor also controls the reading of a flowrate meter 110, which is calibrated to read in units of cubic centimeters of blood per minute.

The microprocessor 102 of FIG. 2 will control the elements of the hemodialysis system of FIG. 1 in accordance with a single needle control program or a double needle control program stored in the memory 104. Mode of operation, and hence program selection, is accomplished by setting mode switch 112 for the desired mode. When the single needle mode is selected, the system operates using all of the elements shown in FIG. 1.

In the single needle mode, the control program causes the arterial and venous pumps to operate alternately during an arterial (blood withdrawal) phase and a venous (blood return) phase, respectively. During the arterial phase, the arterial pump 20 pumps blood through the dialyzer 40 and into the venous drip chamber 50 and the accumulator bag 70. Since the accumulator bag 70 is made of collapsible vinyl, it will fill freely with blood, generating substantially no back pressure at the outlet of the dialyzer. Eventually a point will be reached at which the bag will become full and taut, and blood pressure at the outlet of the dialyzer will begin to rise. This pressure use is sensed by the pressure transducer 56, which signals the microprocessor accordingly. When the dialyzer outlet pressure reaches a predetermined level, the controller 100 stops the operation of the arterial pump 20 and starts the venous pump 80.

The venous pump 80 is operated for a predetermined number of pump turns, which is monitored by the controller by receipt of information from the venous pump slot encoder. Since each pump turn corresponds to the transmission of a known volume of blood, operating the venous pump for a predetermined number of turns will return a predetermined amount of blood through the needle 10. In a working embodiment of the present invention, the pump motor turns the roller of the pump through a reduction system such that the motor shaft, and hence the slotted disc 120, rotates 49 times for each turn of the pump roller. When the disc contains 20 slots around its perimeter, 980 pulses will be produced by the slot encoder during one pump roller turn. Thus, fractions of roller turns, and hence small units of blood flow, may be measured precisely. Once the venous pump has completed a predetermined number of pump turns, the venous pump is stopped and the arterial pump is turned on to begin another arterial phase.

The foregoing technique of system operation, in which the arterial blood pump is controlled as a function of blood pressure and the venous blood pump is controlled as a function of pump turns, is described more fully in concurrently filed U.S. patent application Ser. No. 423,328, entitled "Dual Phase Blood Flow System And Method Of Operation".

When the arrangement of FIGS. 1 and 2 is operated in the single needle mode, both the speeds of the two blood pumps and the ratio of the speeds of the individual blood pumps may be controlled. When the speeds of the two pumps are controlled simultaneously, the blood flowrate through the system is affected. Hence, when the speeds of the two pumps are simultaneously increased, the blood flowrate, as indicated on the flowrate meter 110, will increase. Control of the ratio of the speeds of the individual blood pumps advantageously allows the system to operate in a manner which will reduce the possibility of fistula occlusion. In the preferred embodiment of the present invention shown in FIG. 2, the ratio control 114 will control the venous-to-arterial pump speeds from a ratio of 1:1 to a ratio of 2:1. At a 1:1 ratio, the speeds of the two pumps are controlled to be the same, and at a 2:1 ratio the speed of the venous pump is twice that of the arterial pump. At the 2:1 ratio, the arterial pump will withdraw blood from the patient's fistula at a relatively low rate, which should tend to reduce the possibility that the fistula will collapse.

When system operation in the single needle mode is commenced, it is preferable to first set the ratio control 114 to the desired pump speed ratio. Then, when hemodialysis begins, the blood flowrate as indicated on the flowrate meter 110 is noted. If the flowrate is lower or higher than desired, the speed control 116 is then adjusted, which will cause the flowrate to change. The speed control adjustment is seen to be reflected in a change in the blood flowrate, which is the aspect of operation desired to be controlled, as opposed to actual knowledge of the velocities of the pumps.

For example, assume that system operation commences at an indicated flowrate of 100 cc/min., and that a blood flowrate of 200 cc/min. is desired. The speed control 116 will be adjusted to cause the microprocessor 102 to increase the speeds of the two pumps. The arterial pump will then attain its predetermined pressure threshold in a shorter period of time, and the venous pump will complete its predetermined number of pump turns in a shorter period of time. The net result will be an increase in the number of cubic centimeters of blood processed through the system each minute.

In the single needle mode two blood pumps are required to pump blood in alternately different directions through the single needle. However, in the double needle mode, blood flow is in only one direction through the system, and hence double needle hemodialysis may be performed using only a single blood pump. Thus, when the mode switch 112 is switched to the double needle mode, the controller 100 controls the system with a program that utilizes the arterial blood pump 20 as the only blood pump in the system. The arterial blood pump then operates to withdraw blood from the patient through a first needle, pumps the blood through the arterial drip chamber 30 and the dialyzer 40, into the venous drip chamber 50 and back to the patient through a second needle. Since there is no cycling between two pumps, the flexible accumulator bag 70 and the solid state pressure transducer, which are used to detect the pressure at which the pump changeover occur in the single needle mode, are not used in the double needle mode. The mechanical venous and arterial pressure gages are still used in the double needle mode to guard against the development of undesirable blood pressures in the system and to insure that proper transmembrane pressures are maintained in the dialyzer.

In the double needle mode, the venous to arterial ratio control 114 is unnecessary, since only one blood pump is operating. The speed control 116 is used as in the single needle mode to control the speed of the arterial pump, and hence the blood flowrate. Once the system is operating in the double needle mode the speed control may be adjusted while observing the flowrate indicated or the flowrate meter 110. The speed control 116 is adjusted until the desired blood flowrate is indicated on the meter 110.

The previously mentioned Extracorporeal SPS System Model DM-350, a double needle hemodialysis system which employs only a single blood pump, may be modified to perform both single and double needle hemodialysis by the addition of the module 300 shown in FIG. 3. The module 300 includes a venous blood pump 80 mounted on the front surface of the module. The air/foam detector 90 is located on the side of the module, and includes blood tubing clamps 314 and 316. The upper clamp 314 contains sensors such as ultrasonic transducers to detect the presence of air or bubbles in the blood line (not shown). The positive and negative pressure pillow switches 14 and 72 are also located on the side of the module. The positive pressure pillow switch includes two blood tubing clamps 324 and 326 spaced above and below a pushbutton switch 18, which detects undesirably low pressures in the blood tubing pillow held against it. The negative pressure pillow switch includes blood tubing clamps 334 and 336, located above and below a pushbutton switch 76, the latter acting to sense the presence of undesirably high blood pressure in the blood tubing pillow strapped across it.

On the top of the module are a series of LED indicators shown at 350, which indicate fault conditions in the system. The appropriate indicators are lit under control of the microprocessor 102 when fault conditions are sensed. A lighted alarm and mute/reset switch 340 is used to reset the system after a fault has been corrected and system operation is resumed. The venous to arterial ratio control 114 and the mode switch 112 are also located on top of the module. A separate LED indicator 352 lights when the single needle mode is selected by the mode switch 112.

The module 300 is suitable for mounting on the front of the SPS DM-350 hemodialysis unit. The electrical connections shown in FIG. 2, including power cable 140 and a ribbon cable and connector 360 shown in FIG. 3, must then be made to power the module and to connect the components on the module to the controller which is located in the SPS unit. The speed control 116 of FIG. 2 is located on the SPS unit and is already connected to the controller, as in the blood flowrate meter 110. Finally, the controller in the SPS system must be modified with a new input/output structure and memory 104 containing both the single and double needle operating programs, if the controller already in the SPS unit is only a double needle mode device. Such modification is accomplished by the simple replacement of printed circuit boards.

We claim:

1. A hemodialysis system for a patient which is capable of operation in either a single needle mode or a double needle mode comprising:
    a first arterial blood pump having an input adapted to withdraw blood from said patient and an output, said arterial blood pump being the only operational blood pump in said system during said double needle mode;
    a dialyzer having an input coupled to the output of said arterial blood pump and an output;
    means, having an input coupled to the output of said dialyzer and an output for returning blood to said patient, said means comprising, during said single needle mode, a second venous blood pump;
    a pump speed control coupled to the operational pumps during said respective modes for establishing pump speeds during said modes;
    control means, coupled to said pump speed control and to said operational pumps during said respective modes, for continuously activating said arterial blood pump during said double needle mode, and for alternately activating said arterial and venous pumps during said single needle mode; and
    a pump speed ratio control coupled to said control means for setting the speed ratio of said venous and arterial blood pumps, wherein said control means is responsive to the setting of said ratio control only during said single needle mode.

2. The hemodialysis system of claim 1, further comprising:
    a pressure monitor coupled to the output of said dialyzer for measuring the blood pressure thereat,
    wherein said control means is responsive to the measurement of blood pressure by said monitor for alternately activating said pumps during said single needle mode.

3. A unit for modifying a single blood pump hemodialysis system including a dialyzer and a pump controller for operation as a double blood pump hemodialysis system comprising:
    a venous blood pump adapted for connection by a blood tubing set to the output of said dialyzer;
    a pump speed ratio control for controlling the relative speeds of said single blood pump and said venous blood pump;
    first and second pillow switches for monitoring blood pressures at the inputs of said respective blood pumps;
    means for providing a source of energization potential to said unit from said single blood pump hemodialysis system; and
    means for connecting said unit, including said venous blood pump and said pump speed ratio control, to said pump controller.

4. The unit of claim 3, further comprising:
    means, coupled to said pump controller, for selecting either single blood pump hemodialysis operation or double blood pump hemodialysis operation.

5. The unit of claim 4, further comprising:
    a plurality of indicators, coupled to said pump controller, for indicating the status of operation during said double blood pump hemodialysis operation.

6. The unit of claim 5, further comprising:
    an air/foam detector adapted to detect the presence of air or foam in the blood tubing at the output of said venous blood pump.

* * * * *